(12) United States Patent
Stopek et al.

(10) Patent No.: US 10,448,861 B2
(45) Date of Patent: *Oct. 22, 2019

(54) SYSTEM AND METHOD FOR LIGHT BASED LUNG VISUALIZATION

(71) Applicant: COVIDIEN LP, Mansfield, MA (US)

(72) Inventors: Joshua B. Stopek, Minneapolis, MN (US); Joseph D. Brannan, Erie, CO (US); William J. Dickhans, Longmont, CO (US); Casey M. Ladtkow, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,744

(22) Filed: Aug. 27, 2014

(65) Prior Publication Data
US 2015/0073268 A1 Mar. 12, 2015

Related U.S. Application Data

(60) Provisional application No. 62/041,893, filed on Aug. 26, 2014, provisional application No. 62/041,800, (Continued)

(51) Int. Cl.
*A61B 5/00* (2006.01)
*A61B 5/08* (2006.01)
(Continued)

(52) U.S. Cl.
CPC .............. *A61B 5/08* (2013.01); *A61B 1/2676* (2013.01); *A61B 5/0084* (2013.01); *A61B 5/061* (2013.01);
(Continued)

(58) Field of Classification Search
CPC ....................................................... A61B 5/08
(Continued)

(56) References Cited

U.S. PATENT DOCUMENTS

| 5,244,462 A | 9/1993 | Delahuerga et al. |
| 5,531,520 A | 7/1996 | Grimson et al. |
| (Continued) | | |

FOREIGN PATENT DOCUMENTS

| CN | 1628602 A | 6/2005 |
| CN | 102883651 A | 1/2013 |
| (Continued) | | |

OTHER PUBLICATIONS

Deguchi, "A method for bronchoscope tracking by combining a position sensor and image registration", Computer Aided Surgery, 11(3), 2006, pp. 109-117.*

(Continued)

*Primary Examiner* — Tse W Chen
*Assistant Examiner* — Joanne M Hoffman (57) ABSTRACT

A system for light based interrogation of a lung includes a memory, an electromagnetic (EM) board, an extended working channel (EWC), an EM sensor, a light source, a light receptor and a processor. The memory stores a 3D model and a pathway plan of a luminal network and the EM board generates an EM field. The EWC navigates a luminal network of a patient toward a target in accordance with the pathway plan and the EM sensor extends distally from a distal end of the EWC and is configured to sense the EM field. The light source is located at or around the EWC and emits light, and the light receptor is located at or around the EWC and is configured to sense reflected light from airway of the luminal network. The processor converts the reflected light into light based data and identifies a type or density of tissue.

18 Claims, 8 Drawing Sheets

Related U.S. Application Data filed on Aug. 26, 2014, provisional application No. 61/874,881, filed on Sep. 6, 2013.

(51) Int. Cl.
*A61B 5/06* (2006.01)
*A61B 5/113* (2006.01)
*A61B 1/267* (2006.01)

(52) U.S. Cl.
CPC ............. *A61B 5/066* (2013.01); *A61B 5/113* (2013.01); *A61B 5/7207* (2013.01); *A61B 5/7425* (2013.01); *A61B 5/0066* (2013.01); *A61B 5/0075* (2013.01); *A61B 5/062* (2013.01)

(58) Field of Classification Search
USPC ........................................................ 600/424
See application file for complete search history.

(56) References Cited

U.S. PATENT DOCUMENTS

| | | | |
|---|---|---|---|
| 5,569,289 | A | 10/1996 | Yoon |
| 5,633,951 | A | 5/1997 | Moshfeghi |
| 6,379,302 | B1 * | 4/2002 | Kessman ............ A61B 8/0841 600/437 |
| 6,749,606 | B2 | 6/2004 | Keast et al. |
| 7,835,785 | B2 | 11/2010 | Scully et al. |
| 7,883,471 | B2 | 2/2011 | Aljuri et al. |
| 7,889,905 | B2 | 2/2011 | Higgins et al. |
| 7,901,348 | B2 | 3/2011 | Soper et al. |
| 7,985,187 | B2 | 7/2011 | Wibowo et al. |
| 8,357,193 | B2 | 1/2013 | Phan et al. |
| 8,382,662 | B2 | 2/2013 | Soper et al. |
| 8,454,527 | B2 | 6/2013 | Aljuri et al. |
| 8,821,376 | B2 | 9/2014 | Tolkowsky |
| 2005/0107688 | A1 | 5/2005 | Strommer |
| 2005/0182295 | A1 | 8/2005 | Soper et al. |
| 2005/0283067 | A1 | 12/2005 | Sobe |
| 2006/0121488 | A1 * | 6/2006 | Rothstein ............ C07K 14/47 435/6.16 |
| 2006/0287595 | A1 * | 12/2006 | Maschke ............ A61B 1/042 600/424 |
| 2007/0015981 | A1 * | 1/2007 | Benaron ............ A61B 5/412 600/323 |
| 2007/0078334 | A1 | 4/2007 | Scully et al. |
| 2008/0071140 | A1 * | 3/2008 | Gattani ............ A61B 1/0005 600/117 |
| 2008/0118135 | A1 | 5/2008 | Averbuch et al. |
| 2008/0207997 | A1 | 8/2008 | Higgins et al. |
| 2008/0221409 | A1 * | 9/2008 | Hoarau ............ A61B 5/0075 600/310 |
| 2008/0287803 | A1 | 11/2008 | Li et al. |
| 2009/0118727 | A1 | 5/2009 | Pearson et al. |
| 2009/0299352 | A1 | 12/2009 | Zerfas et al. |
| 2010/0145186 | A1 | 6/2010 | McGrath et al. |
| 2010/0280363 | A1 * | 11/2010 | Skarda ............ A61B 1/00135 600/424 |
| 2010/0317964 | A1 | 12/2010 | Hendriks et al. |
| 2011/0184238 | A1 | 7/2011 | Higgins et al. |
| 2011/0207997 | A1 * | 8/2011 | Greenburg ............ A61B 5/05 600/104 |
| 2011/0301438 | A1 | 12/2011 | Sachse et al. |
| 2012/0059248 | A1 * | 3/2012 | Holsing ............ A61B 1/2676 600/424 |
| 2012/0108629 | A1 * | 5/2012 | Jiang .................... A61K 9/0019 514/308 |
| 2012/0197145 | A1 * | 8/2012 | Wu .................... A61B 5/04007 600/509 |
| 2012/0238806 | A1 | 9/2012 | Mangiardi et al. |
| 2012/0289772 | A1 | 11/2012 | O'Connell et al. |
| 2013/0023729 | A1 | 1/2013 | Vazales et al. |
| 2013/0060240 | A1 | 3/2013 | Scheller et al. |
| 2013/0223702 | A1 * | 8/2013 | Holsing ............ A61B 5/113 382/128 |
| 2013/0231557 | A1 | 9/2013 | Li et al. |
| 2014/0105472 | A1 | 4/2014 | Yin et al. |

FOREIGN PATENT DOCUMENTS

| | | |
|---|---|---|
| CN | 102970945 A | 3/2013 |
| CN | 103025262 A | 4/2013 |
| EP | 1929956 A2 | 6/2008 |
| EP | 2238901 A2 | 10/2010 |
| JP | 2002345725 A | 12/2002 |
| JP | 2004008412 A | 1/2004 |
| JP | 2004097537 A | 4/2004 |
| JP | 2005169116 A | 6/2005 |
| JP | 2005177477 A | 7/2005 |
| JP | 2005522274 A | 7/2005 |
| JP | 2005218760 A | 8/2005 |
| JP | 2006130183 A | 5/2006 |
| JP | 2006305361 A | 11/2006 |
| JP | 2008512171 A | 4/2008 |
| JP | 2009142653 A | 7/2009 |
| JP | 2009279171 A | 12/2009 |
| JP | 2009279250 A | 12/2009 |
| JP | 2013519486 A | 5/2013 |
| WO | 0134051 A2 | 5/2001 |
| WO | WO-2006076789 A1 * | 7/2006 ............ A61B 5/06 |
| WO | 2008125910 A2 | 10/2008 |
| WO | 2011062035 A1 | 5/2011 |
| WO | 2016033090 A1 | 3/2016 |

OTHER PUBLICATIONS

Higgins, "3D CT-Video Fusion for Image-Guided Bronchoscopy" Comput Med Imaging Graph, 33(3), 2008 pp. 1-18.*
Higgins, W., Helferty, J., Lu, K., Merrit, S., Rai, L., and Yu, K., "3D CT-Video Fusionfor Image-Guided Bronchoscopy", Comput Med Imaging Graph, 32(3), 2008, pp. 159-173. (Year: 2008).*
Leong, S., Ju, H., Marshall, H., Bowman, R., Yank, I., Ree, A., Saxon, C., and Fong, K.,"Electronnagnetic navigation bronchoscopy: A descriptive analysis", J Thorac Dis, 4(2), 2012, pp. 173-185 (Year: 2012).*
International Search Report issued in corresponding PCT application No. PCT/US2014/053890 dated Nov. 24, 2014.
Randy Hou et al: "Recent advances in optical coherence tomograpy for the diagnoses of lung disorders". Expert Review of Respiratory Medicine, vol. 5, No. 5, Oct. 1, 2011, pp. 711-724.
Pyng Lee et al: "Bronchoscopy in Lung Cancer—Appraisal of Current Technology and for the Future", Journal of Thoracic Oncology, vol. 5, No. 8, Aug. 1, 2010, pp. 1290-1300.
Bojan Zaric et al: "Diagnostic value of autofluorescence bronchoscopy in lung cancer", Thoracic Cancer, vol. 4, No. 1, Feb. 1, 2013, pp. 1-8.
Supplementary European Search Report issued in corresponding EP Application No. 14842292 dated Apr. 11, 2017, 9 pages.
Supplementary European Search Report issued in corresponding EP Application No. 14841710.8, dated Apr. 11, 2017, 12 pages.
Office Action for corresponding Japanese Application No. 2016-540341 dated Jun. 20, 2017, 19 pages.
Japan Electronics and Information Technology Industries Association, Kaitei lyou Choonpa Kiki Handobuku, Japan, Corona, Jan. 20, 1997, p. 15, p. 35. (A part or the whole of the non-patent literature indicated above may not be forwarded due to restrictions arising from law or contract.)
Supplementary European Search Report for corresponding European Application No. 14843010.1 dated Jun. 26, 2017, 13 pages.
Supplementary European Search Report issued in corresponding Application No. EP 14 84 2874, dated Apr. 12, 2017.
Luo et al., Beyond Current Guided Bronchoscopy: A robust and real-time bronchoscopic ultrasound navigation system in: Lecture Notes in Computer Science (LNCS): Medical Image Computing and Computer-Assisted Intervention—MICCAI 2013, vol. 8149, pp. 388-395 (2013).

(56) References Cited

OTHER PUBLICATIONS

Krimsky et al., Bronchoscopy and the peripheral nodule in the age of lung cancer screening and targeted therapies, Current Respiratory Care Reports, vol. 1, No. 1, Jan. 25, 2012, pp. 67-71.
Herth, Bronchoscopic techniques in diagnosis and staging of lung cancer, Breathe, vol. 7, No. 4, Jun. 1, 2011, pp. 329, 332.
Schwarz, Yehuda, MD, FCCP, "Electromagnetic Navigation", Clinics in Chest Medicine, vol. 31, No. 1, Mar. 1, 2010, pp. 65-73, 10 pages.
Supplementary European Search Report issued in corresponding Application No. EP 14842294, dated Apr. 11, 2017, 12 pages.
Chinese Office Action dated Aug. 18, 2017, issued in CN Application No. 201480057462.5.
Office Action for corresponding Chinese Application No. 201480056082.X dated May 25, 2017.
Office Action for corresponding Chinese Application No. 201480056085.3 dated Aug. 2, 2017.
Japanese Office Action dated Mar. 20, 2018 and issued in corresponding Japanese Patent Application No. 2016-540343 together with English translation.
Chinese Office Action dated Apr. 17, 2018 and issued in corresponding Chinese Patent Application No. 201480056085.3, together with English translation.
Chinese Office Action dated Feb. 11, 2018 and issued in Chinese Patent Application No. 201480056082.X together with English translation.
Australian Examination Report dated May 14, 2018 in corresponding Australian Patent Application No. 2014315356.
Australian Examination Report dated May 9, 2018 in corresponding Australian Patent Application No. 2014315359.
Australian Examination Report dated May 14, 2018 in corresponding Australian Patent Application No. 2014315359.
Australian Examination Report dated May 21, 2018 in corresponding Australian Patent Application No. 2014317930.
CN Office Action dated Sep. 19, 2018 in corresponding CN Patent Application No. 201480056085.3, with English translation.
Australian Examination Report dated Jun. 1, 2018 in corresponding Australian Patent Application No. 2014315371.
Japanese Office Action dated Jun. 19, 2018 and issued in corresponding Japanese Patent Application No. 2016-540345 with English translation.
Japanese Office Action dated May 29, 2018 and issued in corresponding Japanese Patent Application No. 2016-540346 with English translation.
Australian Examination Report dated Jun. 1, 2018 and issued in corresponding Australian Patent Application No. 2014315366.
CN Office Action dated Sep. 7, 2018 in corresponding CN Patent Application No. 201480056082.X, with English translation.
Communication pursuant to Article 94(3) EPC and accompanying pages issued by the European Patent Office dated Oct. 29, 2018 in corresponding European Patent Application No. 14841710.8.
Australian Examination Report dated Oct. 30, 2018 in corresponding Australian Patent Application No. 2014315371.
European Examination Report dated Oct. 29, 2018 in corresponding European Patent Application No. 14842292.6.
Australian Examination Report dated Oct. 30, 2018 in corresponding Australian Patent Application No. 2014315366.
Notification of the Fourth Office Action issued by the State Intellectual Property Office of the People's Republic of China dated Apr. 1, 2019 in corresponding Chinese Patent Application No. 201480056082.X, with English translation.
Notification of the Fourth Office Action issued by the China National Intellectual Property Administration dated Apr. 16, 2019 in corresponding Chinese Patent Application No. 201480056085.3, with English translation.

* cited by examiner

SYSTEM AND METHOD FOR LIGHT BASED LUNG VISUALIZATION

CROSS-REFERENCE TO RELATED APPLICATIONS

This application claims priority to and the benefit of U.S. Provisional Patent Application No. 61/874,881, filed on Sep. 6, 2013; U.S. Provisional Patent Application No. 62/041,893, filed on Aug. 26, 2014; and U.S. Provisional Patent Application No. 62/041,800, filed on Aug. 26, 2014. The entire contents of each of these applications is incorporated herein by reference.

This application is related to U.S. patent application Ser. No. 14/469,757, filed on Aug. 27, 2014.

BACKGROUND

Technical Field

The present disclosure relates to systems and methods for light based visualization of a lung. More particularly, the present disclosure relates to systems and methods that augment light based visible images of an airway of a lung to images obtained by other imaging modality and identify a type of lung tissue.

Discussion of Related Art

Standard of care for lung diseases, such as asthma, chronic obstructive pulmonary disease (COPD), and chronic obstructive lung disease (COLD), or for lung-related diseases has been focused largely on medical and/or drug management which are highly invasive to patients in general. For example, it has been reported for decades that lung denervation via localized and invasive means (e.g., surgery) may provide therapeutic benefit for asthma or emphysema.

Electromagnetic navigation (EMN) has helped expand the possibilities of treatment of luminal networks such as the lungs. EMN relies on non-invasive imaging technologies, such as computed tomography (CT) scanning, magnetic resonance imaging (MRI), or fluoroscopic technologies. EMN in combination with these non-invasive imaging technologies has been also used to identify a location of a target and to help clinicians navigate a luminal network of the lung to the target. However, images generated by these non-invasive imaging technologies have been unable to provide a resolution sufficient to identify features such locations of nerves that run parallel to the luminal network. Further, when a treatment is performed, additional images using these non-invasive imaging technologies must have been performed to determine whether the treatment has been complete. That increases the number of exposures of harmful X-rays or substances to the patient and costs of treatments. Still further, it is a continuous desire to greater resolution of the area being treated. Accordingly, there is an ongoing need for an imaging modality, which provides greater resolution and is clinically efficient in operation.

SUMMARY

In an aspect, the present disclosure features a system for light based interrogation of a lung. The system includes a memory, an electromagnetic (EM) board, an extended working channel (EWC), an EM sensor, a light source, a light receptor, and a processor. The memory stores a 3D model of a luminal network and a pathway plan of a luminal network, and the EM board is configured to generate an EM field. The EWC navigates a luminal network of a patient toward a target in accordance with the pathway plan and the EM sensor extends distally from a distal end of the EWC and is configured to sense the EM field. The light source is located at or around the EWC and is configured to emit light, and the light receptor is located at or around the EWC and is configured to sense reflected light from airway of the luminal network. The processor is configured to convert the reflected light into light based data and is configured to identify a type or density of tissue, identify the presence of one or more blood vessel, generate visible images, or integrate the light based data with the 3D model.

In an aspect, the system further includes a display device configured to display the integrated light based data with the 3D model. The display is further configured to display a status based on the location of the EM sensor. The status may indicate whether the EM sensor is located at a not-in-target location, the target, or a location adjacent to healthy tissue, and whether treatment of the target is complete. The generated images show inside of the luminal network.

In an aspect, a resolution of the generated visual images is finer than a resolution of the 3D model.

In another aspect, the light source and the light receptor are located at or around a distal end of the EWC.

In another aspect, a location of integration of the generated images is based on the location of the EM sensor in the 3D model.

In another aspect, the processor is further configured to determine whether a treatment device at the target based on the light based data.

In yet another aspect, the processor is further configured to determine a sufficiency of treatment based on a density of the target according to the light based data.

In yet another aspect, the processor is further configured to determine a sufficiency of treatment based on a change in fluorescent color of the target which is dyed with a fluorescent dye.

In yet still another aspect, the processor performs a spectroscopy analysis using a predictive algorithm based on reflection patterns of lung tissue.

In another aspect, the light source and the light receptor are integrated into a confocal imaging device or an optical coherence tomographic device.

In another aspect, the processor is further configured to determine an offset between the EM sensor and the light receptor. Integration of the light based data with the 3D model is based on the offset.

In another aspect, the system further includes a plurality of reference sensors located on a patient and configured to recognize a breathing pattern of the patient. The system further includes a tracking device configured to identify a location of the EM sensor by compensating for patient's breathing based on the breathing pattern.

In another aspect, the generated images are selectively fused to create a composite image data set with the 3D model.

In yet another aspect, the emitted light wavelength ranges from 400 nanometer to 700 nanometer.

In yet still another aspect, the light source is a light-emitting-diode (LED), laser, incandescent light bulb, or a fluorescent light bulb.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

The present disclosure is related to systems and methods for visualizing the airway of a lung using light-based imaging modalities which provide a sufficient resolution to identify and locate a target for diagnostic, navigation, and treatment purposes. Light-based imaging, particularly in conjunction with non-invasive imaging can provide a greater resolution and enable luminal network mapping and target identification. Further, additional clarity is provided with respect to tissue adjacent identified targets which can result in different treatment options being considered to avoid adversely affecting the adjacent tissue. Still further, the use of light-based imaging in conjunction with treatment can provide detailed imaging for post treatment analysis and identification of sufficiency of treatment. Although the present disclosure will be described in terms of specific illustrative embodiments, it will be readily apparent to those skilled in this art that various modifications, rearrangements, and substitutions may be made without departing from the spirit of the present disclosure. The scope of the present disclosure is defined by the claims appended to this disclosure.

Figure 1:
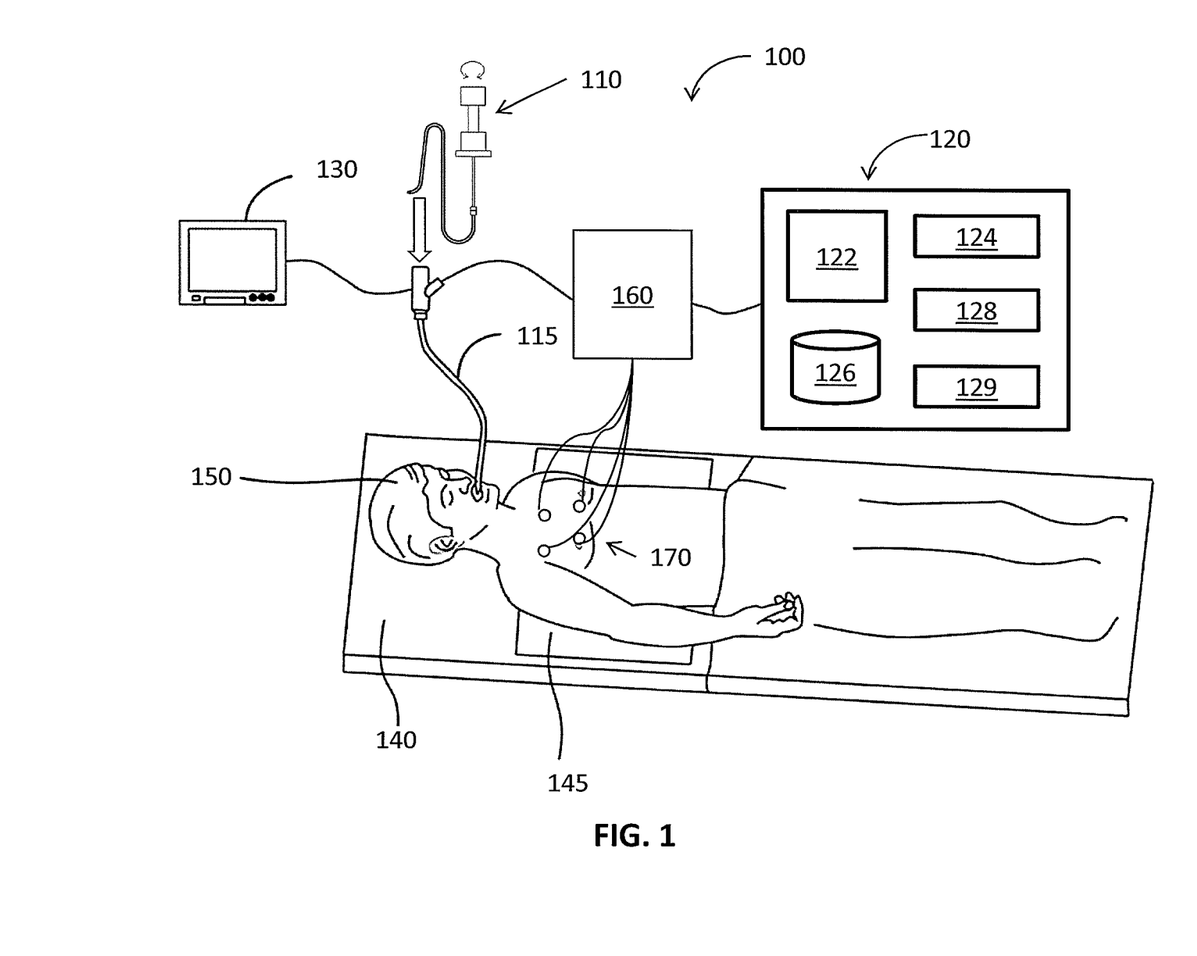
FIG. 1 is a perspective view of a system for light-based visualization of a lung in accordance with an embodiment of the present disclosure.

FIG. 1 illustrates an electromagnetic navigation (EMN) system 100, which is configured to augment CT, MRI, or fluoroscopic images, with light-based image data assisting in navigation through a luminal network of a patient's lung to a target. One such ENM system may be the ELECTROMAGNETIC NAVIGATION BRONCHOSCOPY® system currently sold by Covidien LP. The EMN system 100 includes a catheter guide assembly 110, a bronchoscope 115, a computing device 120, a monitoring device 130, an EM board 140, a tracking device 160, and reference sensors 170. The bronchoscope 115 is operatively coupled to the computing device 120 and the monitoring device 130 via a wired connection (as shown in FIG. 1) or wireless connection (not shown).

The bronchoscope 115 is inserted into the mouth of a patient 150 and captures images of the luminal network of the lung. In the EMN system 100, inserted into the bronchoscope 115 is a catheter guide assembly 110 for achieving access to the periphery of the luminal network of the patient 150. The catheter guide assembly 110 may include an extended working channel (EWC) 230 into which a locatable guide catheter (LG) 220 with the EM sensor 265 (FIG. 2B) at the distal tip is inserted. The EWC 230, the LG 220, and an EM sensor 255 are used to navigate through the luminal network of the lung as described in greater detail below.

The computing device 120, such as, a laptop, desktop, tablet, or other similar computing device, includes a display 122, one or more processors 124, memory 126, a network card 128, and an input device 129. The EMN system 100 may also include multiple computing devices, wherein the multiple computing devices are employed for planning, treatment, visualization, or helping clinicians in a manner suitable for medical operations. The display 122 may be touch-sensitive and/or voice-activated, enabling the display 122 to serve as both input and output devices. The display 122 may display two dimensional (2D) images or three dimensional (3D) model of a lung to locate and identify a portion of the lung that displays symptoms of lung diseases. The generation of such images and models is described in greater detail below. The display 122 may further display options to select, add, and remove a target to be treated and settable items for the visualization of the lung. In an aspect, the display 122 may also display the location of the catheter guide assembly 110 in the luminal network of the lung based on the 2D images or 3D model of the lung. For ease of description not intended to be limiting on the scope of this disclosure, a 3D model is described in detail below but one of skill in the art will recognize that similar features and tasks can be accomplished with 2D models and images.

The one or more processors 124 execute computer-executable instructions. The processors 124 may perform image-processing functions so that the 3D model of the lung can be displayed on the display 122. In embodiments, the computing device 120 may further include a separate graphic accelerator (not shown) that performs only the image-processing functions so that the one or more processors 124 may be available for other programs. The memory 126 stores data and programs. For example, data may be image data for the 3D model or any other related data such as patients' medical records, prescriptions and/or history of the patient's diseases.

One type of programs stored in the memory 126 is a 3D model and pathway planning software module (planning software). An example of the 3D model generation and pathway planning software may be the ILOGIC® planning suite currently sold by Covidien LP. When image data of a patient, which is typically in digital imaging and communications in medicine (DICOM) format, from for example a CT image data set (or an image data set by other imaging modality) is imported into the planning software, a 3D model of the bronchial tree is generated. In an aspect, imaging may be done by CT imaging, magnetic resonance imaging (MRI), functional MRI, X-ray, and/or any other imaging modalities. To generate the 3D model, the planning software employs segmentation, surface rendering, and/or volume rendering. The planning software then allows for the 3D model to be sliced or manipulated into a number of different views including axial, coronal, and sagittal views that are commonly used to review the original image data. These different views allow the user to review all of the image data and identify potential targets in the images.

Once a target is identified, the software enters into a pathway planning module. The pathway planning module develops a pathway plan to achieve access to the targets and the pathway plan pin-points the location and identifies the coordinates of the target such that they can be arrived at using the EMN system 100, and particularly the catheter guide assembly 110 together with the EWC 230 and the LG 220. The pathway planning module guides a clinician through a series of steps to develop a pathway plan for export and later use during navigation to the target in the patient 150. The term, clinician, may include doctor, surgeon, nurse, medical assistant, or any user of the pathway planning module involved in planning, performing, monitoring and/or supervising a medical procedure.

Details of these processes and the pathway planning module can be found in commonly assigned U.S. Patent Application No. 62/035,863 filed Aug. 11, 2014 entitled "Treatment procedure planning system and method" and U.S. patent application Ser. No. 13/838,805 filed Jun. 21, 2013, and entitled "Pathway planning system and method," the entire contents of each of which are incorporated in this disclosure by reference. Such pathway planning modules permit clinicians to view individual slices of the CT image data set and to identify one or more targets. These targets may be, for example, lesions or the location of a nerve which affects the actions of tissue where lung disease has rendered the lung function compromised.

The memory 126 may store navigation and procedure software which interfaces with the EMN system 100 to provide guidance to the clinician and provide a representation of the planned pathway on the 3D model and 2D images derived from the 3D model. An example of such navigation software is the ILOGIC® navigation and procedure suite sold by Covidien LP. In practice, the location of the patient 150 in the EM field generated by the EM field generating device 145 must be registered to the 3D model and the 2D images derived from the 3D model. Such registration may be manual or automatic and is described in detail in concurrently filed with this disclosure and commonly assigned U.S. Patent Application 62/020,240 filed by Covidien LP on Jul. 2, 2014, and entitled "System and method for navigating within the lung."

As shown in FIG. 1, the EM board 140 is configured to provide a flat surface for the patient to lie down and includes an EM field generating device 145. When the patient 150 lies down on the EM board 140, the EM field generating device 145 generates an EM field sufficient to surround a portion of the patient 150. The EM sensor 265 at the end of the LG 220 is used to determine the location of the EM sensor 265 in the EM field generated by the EM field generating device 145.

In an embodiment, the EM board 140 may be configured to be operatively coupled with the reference sensors 170 which are located on the chest of the patient 150. The reference sensors 170 move up following the chest while the patient 150 is inhaling and move down following the chest while the patient 150 is exhaling. The movement of the chest of the patient 150 in the EM field is captured by the reference sensors 170 and transmitted to the tracking device 160 so that the breathing pattern of the patient 150 may be recognized. The tracking device 160 also receives outputs of the EM sensor 265, combines both outputs, and compensates the breathing pattern for the location of the EM sensor 265. In this way, the location identified by the EM sensor 265 may be compensated for so that the compensated location of the EM sensor 265 may be synchronized with the 3D model of the lung. Once the patient 150 is registered to the 3D model, the position of the EWC 230 and particularly the LG 220 can be tracked within the EM field generated by the EM field generator 145, and the position of the LG 220 can be depicted in the 3D model or 2D images of the navigation and procedure software.

Figure 2A:
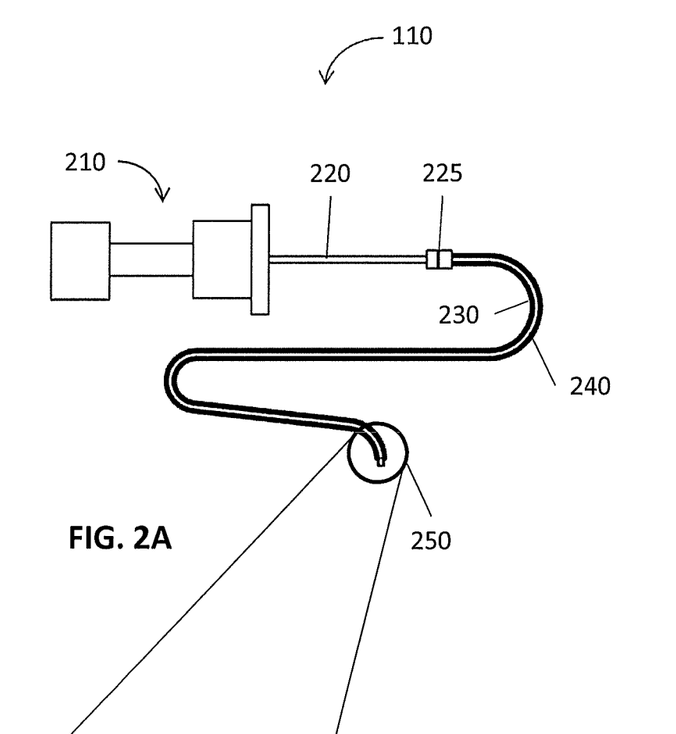
FIG. 2A is a profile view of a catheter guide assembly in accordance with an embodiment of the present disclosure.

FIG. 2A illustrates an embodiment of the catheter guide assembly 110 of FIG. 1. The catheter guide assembly 110 includes a control handle 210. The control handle 210 has an actuator and a selector mechanism for selectively mechanically steering, rotating, and advancing an extended working channel (EWC) 230 or locatable guide catheter (LG) 220 inserted in the EWC 230, meaning that the distal tip 260 of the LG 220 is turning to a direction in accordance with the movement of the control handle 210. A locking mechanism 225 secures the EWC 230 and the LG 220 to one another. Catheter guide assemblies usable with the instant disclosure may be currently marketed and sold by Covidien LP under the name SUPERDIMENSION® Procedure Kits and EDGE™ Procedure Kits. More detailed description of the catheter guide assemblies is made to commonly-owned U.S. patent application Ser. No. 13/836,203 filed on Mar. 15, 2013, by Ladtkow et al. and U.S. Pat. No. 7,233,820, the entire contents of which are hereby incorporated by reference.

Figure 2B:
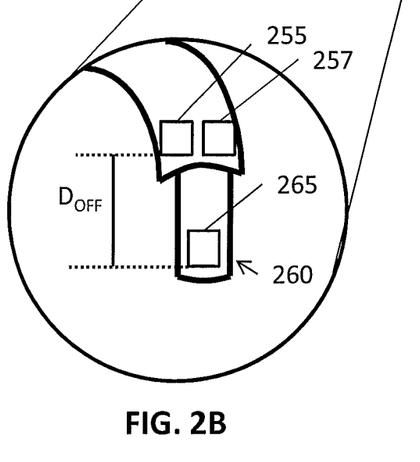
FIG. 2B is an expanded view of the indicated area of detail, which shows a distal tip of an extended working channel of FIG. 2A in accordance with an embodiment of the present disclosure.

FIG. 2B is an expanded view of the distal end 250 of the EWC 230 of FIG. 2A. The light source 255 is located at the distal end 250 of the EWC 230. An EM sensor 265 is located on the distal tip 260 of the LG 220 which is depicted extending beyond the distal end 250 of the EWC 230. As described briefly above, the EM sensor 265 senses the EM field generated by the EM field generating device 145. The sensed EM field is used to identify the location of the EM sensor 265 in accordance with the coordinate system of the EM field. When the location of the EM sensor 265 is determined by the tracking device 160, the computing device 120 compares the location of the EM sensor 265 with the 3D model of the lung and registers the location of the EM sensor 265 into the coordinate system of the 3D model.

For example, when the EM sensor 265 is near at the entrance to the trachea, the EM sensor 265 senses the EM field and the location of the EM sensor 265 is then compared with the trachea portion of the 3D model so that the location of the EM sensor 265 is depicted in the corresponding location of the 3D model and 2D images of the navigation and procedure software. And when the EM sensor 265 is further inserted through the trachea to a location where separate bronchial trees are branched, the distance the EM sensor 265 travels from the entrance of the trachea to the branching location is scaled to match to the corresponding distance in the 3D model and 2D images of the navigation and procedure software. Specifically, when the EM sensor 265 travels along the trachea, the distance is measured in accordance with the coordinate system of the EM field. Since the coordinate system of the EM field is different from the coordinate system of the 3D model, there is a scaling factor to match the coordinate system of the EM field to the coordinate system of the 3D model. Thus, by multiplying a scale factor to the distance the EM sensor 265 travels, the coordinate system of the EM field is synchronized with the coordinate system of the 3D model. In this way, the coordinate system of the EM field may be synchronized with the 3D model and 2D images of the navigation and procedure software. Or other suitable method may be employed to synchronize the coordinate system of the EM field with the coordinate system of the 3D model.

As noted above, the 3D model may not provide a resolution sufficient for guiding the EWC 230 of the catheter guide assembly 110 to a target, meaning that the 3D model becomes blurred or ceases to recognize the luminal network as the EWC 230 approaches a certain point. For example, when CT scan images are taken by 1 mm thick and 1 cm apart by a CT scan device, corresponding 3D model and/or pathway plans may not be able to show full perspective of a target whose size is less than 1 cm or a portion of a luminal network whose diameter is less than 1 cm. Thus, another imaging modality is necessary to find and/or identify a target and/or a terminal bronchial branch, whose size is less than a certain size which CT scan images are unable to show with sufficient details. For this purpose, the memory 126 also stores another program that can process and convert image data captured by an imaging modality associated with the catheter guide assembly 110, as will be described in detail below. This image data may be converted into visual images having sufficient resolutions to identify such targets and terminal bronchial branches or be incorporated into and used to update the data from the CT scans in an effort to provide a greater resolution and fill-in data that was missing in the CT scan.

One such imaging modality is shown in FIG. 2B where light source 255 and a light receptor 257 are depicted on the EWC 230 proximal the distal end. One of skill in the art will recognize that the light source 255 and the light receptor 257 could also be formed on the LG 220, or that more than one of each source and receptor may be employed without departing from the scope of the present disclosure. The light source 255 emits visible light to the airway and the light receptor 257 receives visible light reflected and/or scattered from the tissue of the airway. Generally, the visible light includes electromagnetic waves ranging from 400 nanometer (nm) to 700 nm.

The light source 255 may be the distal end of an optical fiber (not shown), which connects at its proximal end to a light-emitting-diode (LED), incandescent light bulb, fluorescent light bulb, or any suitable source that generates visible light. Similarly, the light receptor 267 may be the distal end of an optical fiber which connects to imaging hardware and software resident on the computing device 120. The imaging hardware may include a photovoltaic cell, photoresistor, photodiode, phototransistor, color coupled charge, confocal mini-probe, or any device suitable to detect light having wavelengths ranging from 400 nm to 700 nm. The optical fibers may be located within the EWC 230, attached to the exterior of the EWC 230, or placed within the inner lumen of the EWC 230.

Different types of lung tissue have different patterns of absorption, scattering, and reflection of visible light at specific frequencies. These patterns may be deterministically used in the spectroscopy analysis using a predictive algorithm to identify a type of tissue. These patterns may be also used to identify a density of tissue, the disease state of the tissue, and the sufficiency of treatment, and to determine whether the light receptor 267 is at a target to be treated. White light may be used for spectroscopy analysis because the white light includes all of the visible range of light. In an aspect, the light-based imaging modality may be optical coherent tomography. In embodiments, the light source 265 and the light receptor 267 may be formed around the EWC 230 and generates a radial view of the airway of the bronchial tree and generates an optical map of the airway.

Figure 5A:
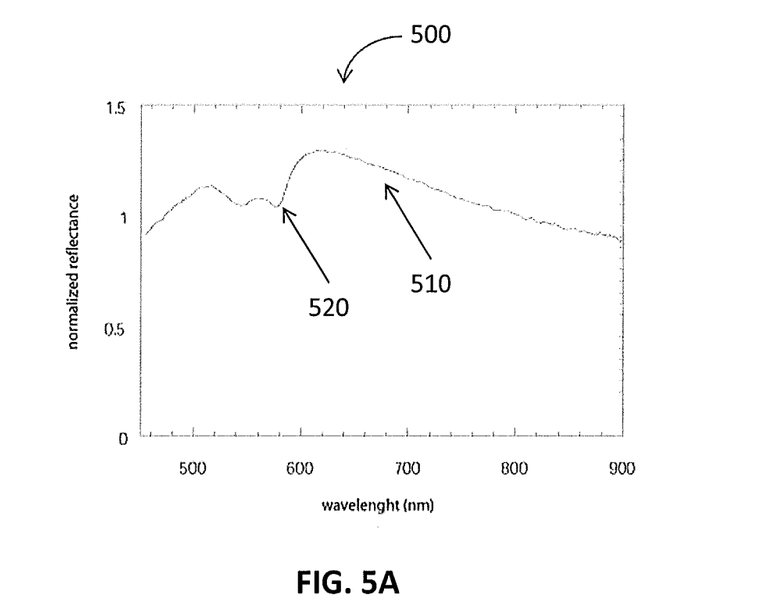
FIG. 5A is a graph illustrating reflection pattern of a lung tissue.

FIG. 5A illustrates reflectance spectroscopy 500 of the bronchial mucosa. The vertical axis represents the normalized reflectance ranging from 0 to 1.5 without a unit and the horizontal axis represents wavelengths ranging from 400 nm to 900 nm. There is a dip 520 in the reflectance spectral signal graph 510, which is near 600 nm because hemoglobin in the blood absorbs light at that frequency. The reflectance spectral signal graph 510 may show reflectance pattern or absorption pattern of normal bronchial mucosa.

Figure 5B:
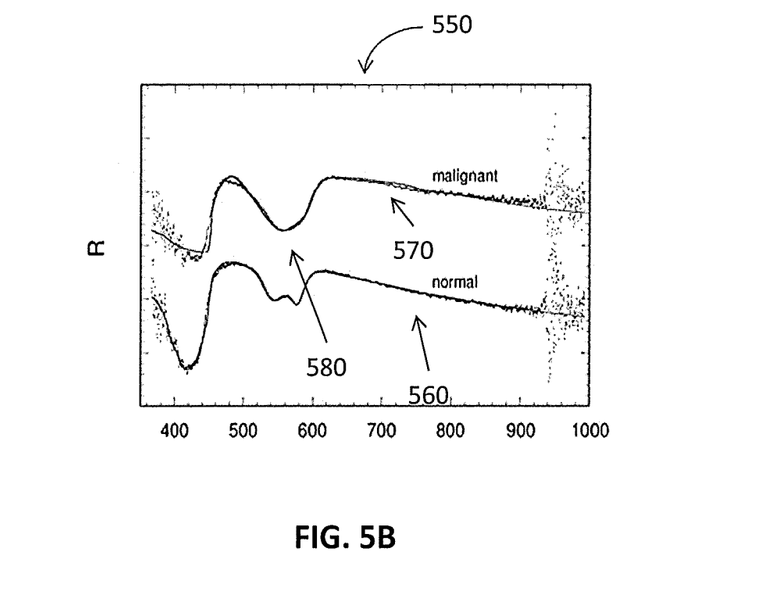
FIG. 5B is a graph illustrating reflection patterns of normal and malignant lung tissues.

FIG. 5B illustrates examples of another reflectance spectral signal graph 550 for normal and malignant bronchial mucosae. As described in FIG. 5A, the vertical axis represents the reflectance pattern without a unit and the horizontal axis represents wavelengths ranging from 300 nm to 1,000 nm. The reflectance spectral signal graph 560 shows the reflectance pattern of normal mucosa and the reflectance spectral signal graph 570 shows the reflectance pattern of malignant mucosa. As apparent in FIG. 5B, the malignant mucosa has a steeper dip 580 near 600 nm than the normal mucosa does. It is evidenced that the malignant mucosa has more blood volume, resulting in more hemoglobin in the lesion, which absorbs more light at that frequency and reflects less light.

Based on the blood content, normal mucosa and malignant mucosa have different patterns of reflectance spectrum when white light is emitted by the light source 255. However, these patterns of reflectance spectrum cannot be readily identifiable to human eyes. Thus, when the light receptor 257 senses reflected light, the computing device 120 performs spectroscopy analysis on the reflected light, identifies a type or density of tissue, and/or determines whether the tissue is malignant. The computing device 120 may augment 3D model or the 2D images derived therefrom with the spectroscopic data.

In an aspect of the present disclosure, fluorescence may be used to identify a target with the spectroscopy using visible light. When a target is identified by the CT or MM scanning, the target may be dyed by using either fluorescent or auto fluorescent dye. In the case of fluorescent dyes, when the light source 255 emits light to a fluorescently dyed lesion, the fluorescent dye radiates a specific frequency response that can be received at the light receptor 257 and detected as different from the response of other un-dyed lung tissue. Similarly, but without the need of the light source 255, auto fluorescent dyes constantly emit a signal at a specific frequency, and these emissions can be received and detected by the light receptor 257. In both cases, the response can be processed and displayed on the display of the computing device 120, thus permitting visualization of the target without requiring spectroscopic analysis.

In embodiments, when a treatment is performed to treat an abnormal tissue of a bronchial tree, the fluorescence color may change along the treatment. In other words, when the treatment is complete, the fluorescent color may disappear or change to a predetermined color. Thus, by inspecting the fluorescent color of the target, a clinician may determine whether the treatment of the target is complete or another treatment is to be made. Generally, when a treatment has been performed, another set of CT or MRI scan needs to be performed to check the level of treatment. However, since the light receptor 257 in combination with the light detecting hardware and software is able to check the fluorescent color of the abnormal tissue, the level of treatment may be checked at the spot without performing another CT scan.

As shown in FIG. 2B, the light source 255 and light receptor 257 separated from the EM sensor 265 by a distance, $D_{OFF}$. This distance, $D_{OFF}$, may be coded into the navigation and procedure software, or measured and set by the clinician, or sensed by the light source 255 and the EM sensor 265. The computing device 120 uses the distance, $D_{OFF}$, to adjust the incorporation of the visible-light data images into the 3D model or 2D images derived therefrom. For example, when the EM sensor 265 is located at the distal tip 260 of the LG 220 and the light receptor 257 is located at or circumscribing the distal end 250 of the EWC 230, and separated by 1 cm distance from each other, the visible light data is offset and integrated into the 3D model or 2D images derived therefrom by a distance in the coordinate system of the 3D model, which corresponds to 1 cm in the coordinate system of the EM field.

When the EWC 230 and the LG 220 reaches a target by manipulation of the catheter guide assembly 110 following the pathway plan, the EM sensor 265 confirms its location at the target and a clinician may visually confirm the location at the target by looking at visual images generated by the light receptor 257. The LG catheter 220 may be removed from the catheter guide assembly 110 and a biopsy tool may be inserted into the EWC 230 to the target to retrieve samples of the target for confirmation of the disease. An anchoring tool may be employed to anchor the EWC 230 at the target. Further, treatment tools such as an ablation catheter may be inserted through the EWC 230 and into the target. The light source 255 and light receptor 257 may be used to confirm that the treatment tool is at the target by visually looking at the light data reflected and/or scattered from the tissue surrounding the treatment tool, which is received by the light receptor 257, or by clinically comparing a spectroscopic image of the target with that of normal or diseased tissue.

Some causes of breathing difficulties are associated with mucus and/or foreign objects in the airway. Visible light data sensed by the light receptor 257 may show mucus and foreign objects in the airway. Thus, when these are found while travelling to the target following the pathway plan, the treatment tool such as a suction tool is used to remove mucus or foreign object in the airway of the lung.

In embodiments, in a pre-treatment step, one or more markers can be placed through the EWC 230 to mark the location of the target. The marker may assist in navigating to a desired location and confirming placement of the EWC 230, particularly after removal of the LG 220 and the EM sensor 265 when the EM navigation features of the present disclosure may not be effective. The marker may give a clinician an ability to re-visit the target after the target has been treated and to collect further samples. The marker may be a fiducial marker, fluorescent dye, or FLUOROGOLD®. In the case of fluorescent dye markers, as described above, light data received at the light receptor 257 may be used to determine sufficiency of treatment, or provide greater clarity as to the exact location of the target. Other markers for marking the location of a target may be employed by those of ordinary skill in the art without departing from the scope of the present disclosure.

Figure 3:
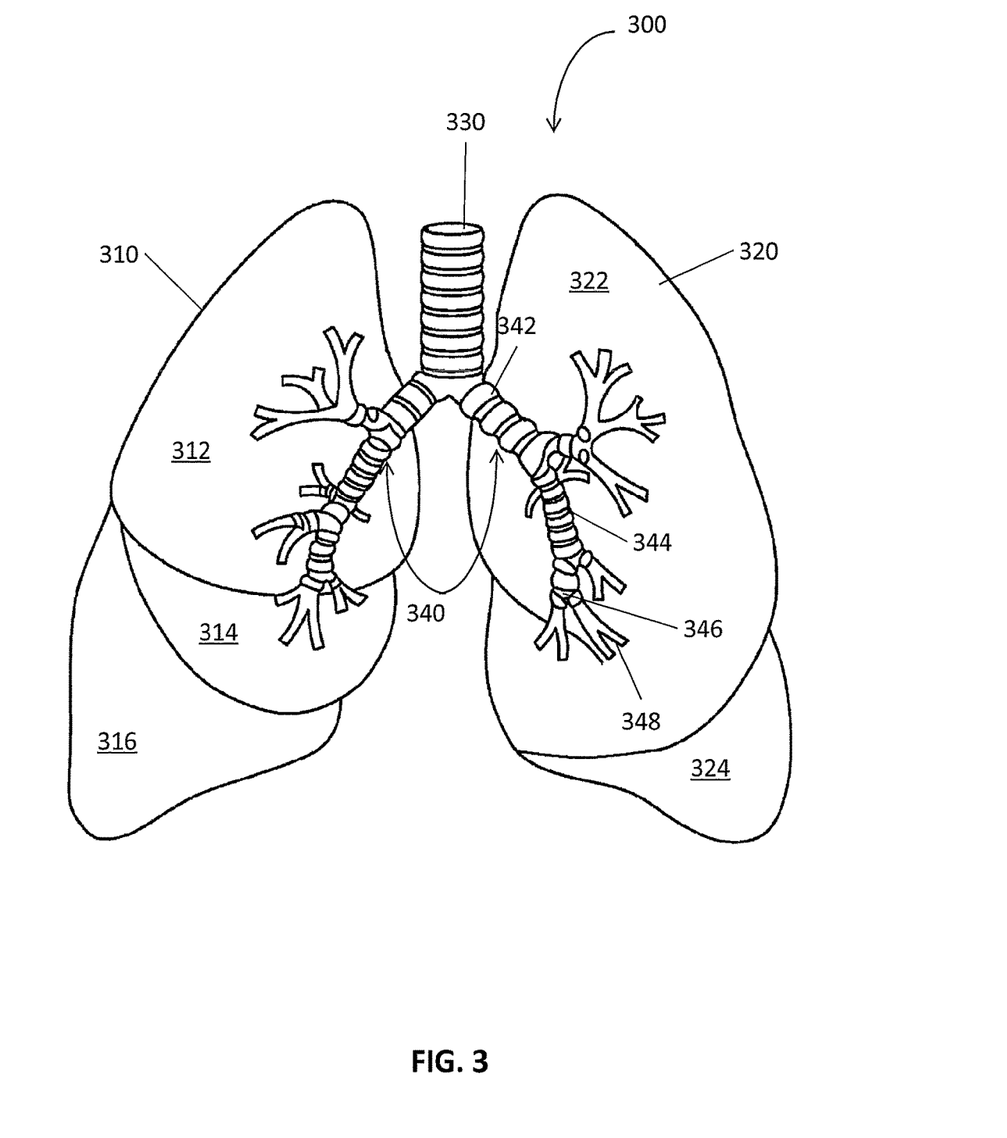
FIG. 3 is an anatomical illustration of a three dimensional model of a lung in accordance with an embodiment of the present disclosure.

FIG. 3 illustrates a 3D model 300 for a patent's bronchial trees and the trachea together with the lung. The 3D model 300 may include information of most of the organs so that a clinician may selectively see particular organs or portions of organs of interest as shown in FIG. 3. In this case, these selected organs are the lungs including right lobe 310, the left lobe 320, the trachea 330 and bronchial trees 340. The right lobe 310 has three sub-lobes, i.e., superior lobe 312, middle lobe 314, and inferior lobe 316, and the left lobe 320 has two sub-lobes, i.e., superior lobe 322 and inferior lobe 324.

The trachea 330 is a tube that connects the pharynx and larynx to the lung 310 and 320. At the lower end of the trachea 330, left or right primary bronchus 342 is divided. Secondary bronchus 344 also divides at the lower end of the primary bronchus 342. The circumference of the primary bronchus 342 is greater than that of the secondary bronchus 344. In the same manner, tertiary bronchus 346 divides at the lower end of the secondary bronchus 344 and terminal bronchiole 348 divides at the lower end of the tertiary bronchus 346. The primary bronchus 342, the secondary bronchus 344, and the tertiary bronchus 346 are supported by cartilaginous plates. However, when the size of the tertiary bronchus 346 becomes smaller and smaller, the cartilaginous plates disappear and outer wall is dominated by smooth muscle. The outer wall of the terminal bronchiole 348 is also dominated by smooth muscle.

Diseased or cancerous cells or simply a target may exist on any bronchial trees, the primary bronchus 342, the secondary bronchus 344, the tertiary bronchus 346, and the terminal bronchioles 348. No matter where a target is located, when a target is too small to be detected by a CT imaging modality, the target may still be detected by the light based interrogation methods as described herein while the EWC 230 with light source 255 and light receptor 257 is navigating toward another target through the luminal network of the lung. The light based data provides greater specificity and greater accuracy in detecting and identifying a target's location in the patient. In accordance with at least one embodiment, the light source 255 and light receptor 257 circumscribe the EWC 230 and are employed to further refine the image data of the lungs by following the pathway plan described above and light based data along the pathway. This light based data may be registered to the CT scan images and/or the 3D model 300 to provide greater clarity with respect to the detection, location, and size of a target. For example, this light based data may also be used diagnostically to help the clinician confirm that all likely targets have been identified or treated completely after treatments.

In addition, when the light receptor 257 captures light based image data, the data is transferred to the computing device 120 wirelessly or via a wired connection. Image data captured by light based techniques are not yet readily viewable by a clinician. The computing device 120 processes and converts the light based image data to an image with which a clinician can identify a type of tissue, diagnose a disease state, or determine a level of treatment.

Figure 4A:
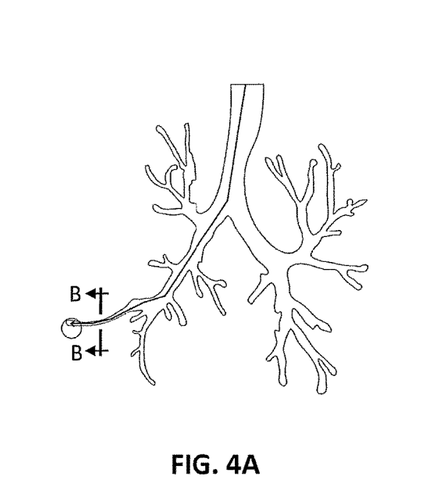
FIG. 4A is an illustration of a pathway from the entry point to the target in accordance with an embodiment of the present disclosure.

FIG. 4A shows a planar view of bronchial trees of the 3D model or of the slices of images of the lung such as the bronchial trees of FIG. 3 and a pathway plan to a target. When a target is located at the tip of the bottom left end of the terminal bronchiole of FIG. 3, a pathway plan shows how to get to the target via the luminal network of the lung.

Figure 4B:
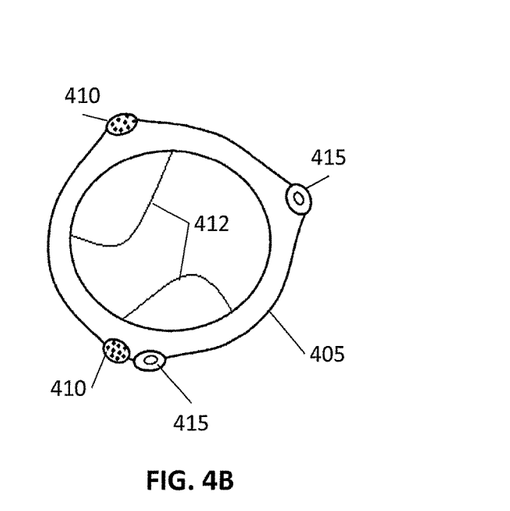
FIG. 4B is a transverse cross-sectional view of the section of the lung of FIG. 4A taken along section line B-B.

FIG. 4B shows an expanded transverse cross-sectional view of the terminal bronchiole of FIG. 4A taken along section line B-B. The terminal bronchiole is surrounded by smooth muscle 405. Nerves 410 and veins 415 are located on the outer wall of the smooth muscle 405. The reference numeral 412 represents swollen smooth muscle, mucus, or a foreign object in the airway. The light-based imaging modality, as described above, provides an inside view of the airways even out to the terminal bronchiole so that foreign object, mucus, or swollen smooth muscle can be visually seen or even the thin nerves 410 and the veins 415 on the smooth muscle 405 can be detected and identified.

Figure 4C:
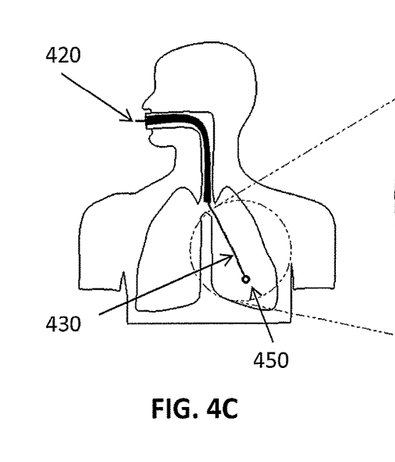
FIG. 4C is an illustration of a catheter guide assembly inserted into a lung following the pathway plan of FIG. 4A.
Figure 4D:
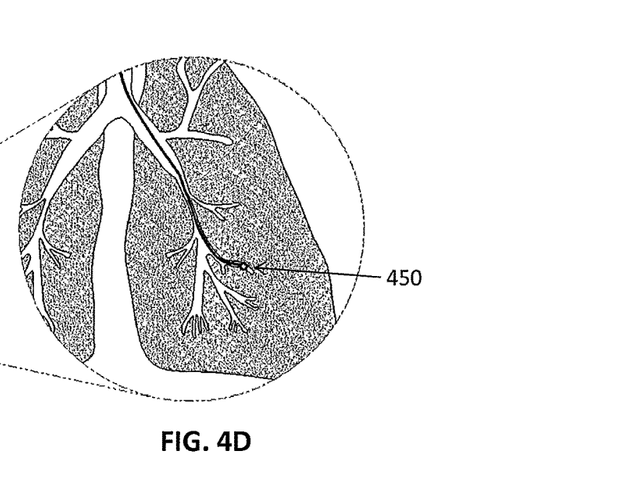
FIG. 4D is an enlarged detail view of the indicated area of detail of FIG. 4C.

FIG. 4C illustrates a bronchoscope 420 with a catheter guide assembly inserted into the lungs via a natural orifice (e.g., the mouth) of a patient toward the target following a pathway plan. When the bronchoscope 420 reaches a certain location of the lung, the bronchoscope 420 becomes wedged and cannot go further into bronchial tree due to the size constraints. Then, the EWC 430 of the catheter guide assembly may be used to navigate the luminal network to a target 450 following the pathway plan, as described above. The EWC 430 is small and thin enough to reach the target 450. FIG. 4D illustrates an enlarged detail view of the circled area of FIG. 4C, where a locatable guide (LG) may stick out of the distal tip of the EWC 430 which navigates the luminal network to the target 450 located at the terminal bronchiole of the lung.

Figure 6A:
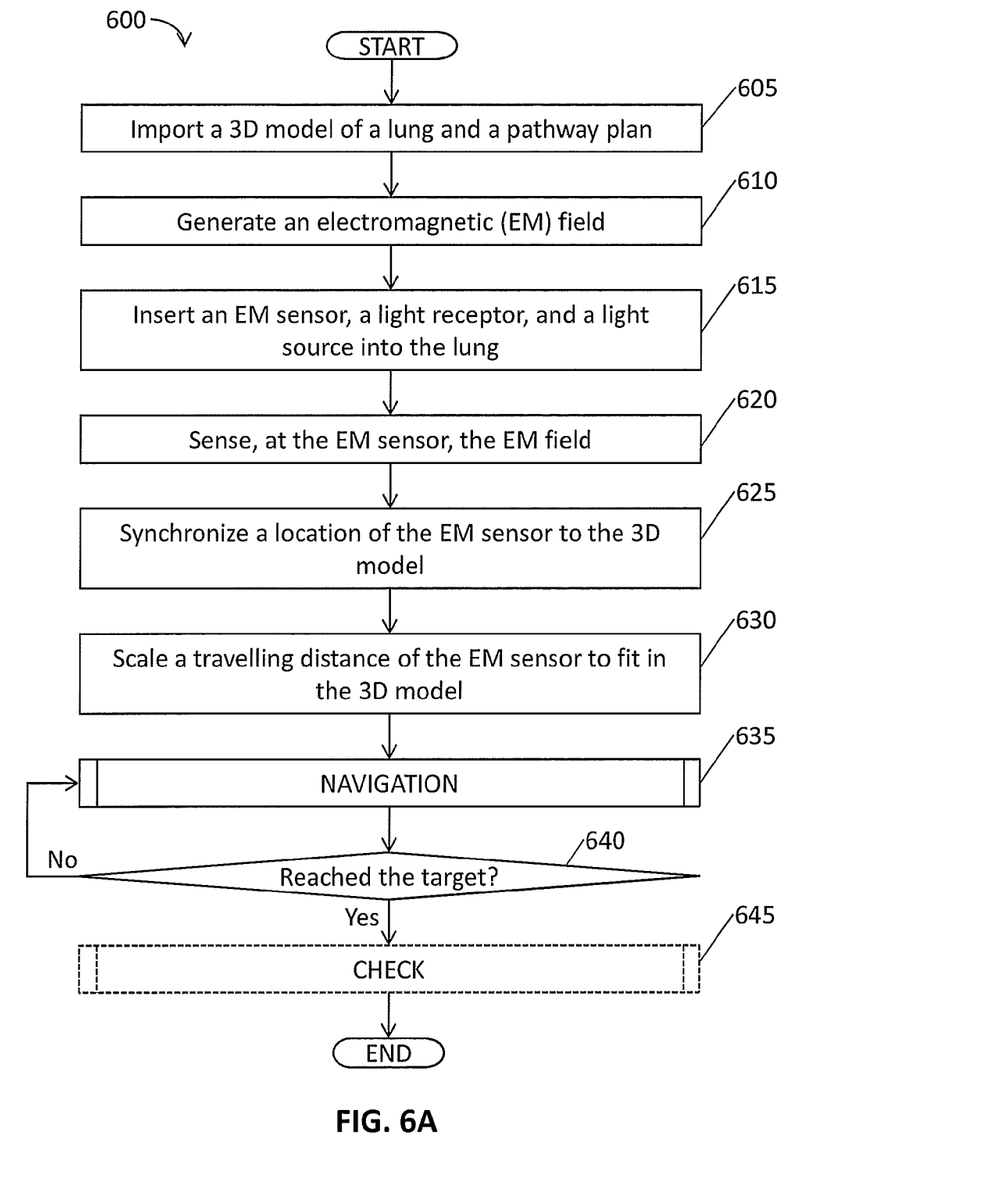
FIG. 6A is a flowchart of a method for visualizing a lung using light in accordance with an embodiment of the present disclosure.

FIG. 6A is a flowchart of a method 600 for visualizing lung tissue using visible light techniques. The method 600 starts at step 605 by importing a 3D model of a lung and a pathway plan to a target into the navigation and procedure software stored on a computer such as the computing device 120 of FIG. 1.

In step 610, an EM field is generated by the EM field generating device 145 of the EM board 140 as shown in FIG. 1. In step 615, the EM sensor 265, the light source 255 and the light receptor 257 are inserted into the lung via a natural orifice or an incision. In an aspect, the EM sensor 265 and the light source 255 and light receptor 257 may be located on the EWC 230 with a distance apart or may be located at different places. For example, the EM sensor 265 may be located at or around the distal tip 260 of the LG 220 and the light source 255 and light receptor 257 may be located at or around the distal end 250 of the EWC 230, or vice versa.

In step 620, the EM sensor 265 senses the EM field and the sensed results are transmitted to the computing device 120. The sensed results are used to calculate a location of the EM sensor 265 in the coordinate system of the EM field. Once the location is calculated, the computing device 120 compares the location of the EM sensor 265 with the 3D model or the 2D images derived therefrom and the pathway plan. In an aspect, the location of the EM sensor 265 may be compensated according to the breathing pattern of the patient, which may be detected by the tracking device 160 and the reference sensors 170 before transmitted to the computing device 120. Thus, the location of the EM sensor 265 may not vary in the coordinate system of the 3D model while the patient inhales or exhales.

In step 625, the location of the EM sensor 265 is synchronized with the 3D model and the 2D images derived therefrom. This location may be the starting location of the 3D model, or the entrance of the trachea of the 3D model. Even though the location is synchronized, the actual movement of the EM sensor 265 is not synchronized to the 3D model yet, here.

The EM sensor 265 travels a certain distance (e.g., from the entrance of the trachea to the branching point at the bottom of the trachea). This distance may be measured in the coordinate system of the EM field after the EM sensor 265 starts to sense the EM field. In step 630, the travelling distance by the EM sensor 265 according to the coordinate system of the EM field may be scaled so that the scaled distance is matched to the coordinate system of the 3D model. After this step, the location and the movement of the EM sensor 265 are substantially mapped into the 3D model. This is the synchronization or registration of the patient to the 3D model and the 2D images derived therefrom.

In step 635, the EM sensor 265, the LG 220, and the EWC 230 navigate the luminal network of the lung to the target following the pathway plan. In step 640, it is determined whether the EM sensor 265 reached the target. If it is determined that the EM sensor 265 has not reach the target, navigation step 635 continues until the target is reached following the pathway plan.

In embodiments, when it is determined that the target is reached in step 640, step 645 may be performed to interrogate the target with the light based techniques described herein to confirm its location. In addition, interrogation may be employed after treatment to ensure sufficiency of treatment. Step 645 is described in further detail in FIG. 6C below.

Figure 6B:
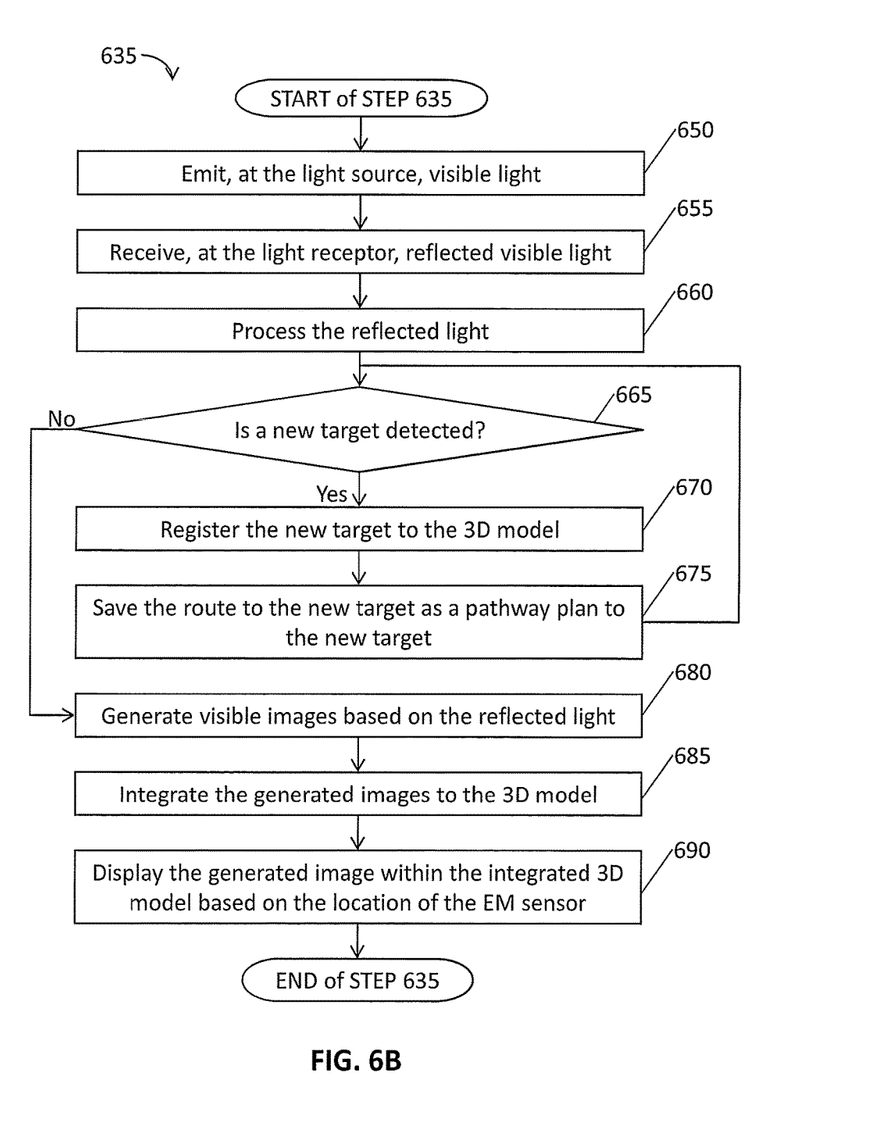
FIG. 6B is a flowchart of a method for navigation to the target in accordance with an embodiment of the present disclosure.

FIG. 6B shows detail steps of navigation to the target, step 635 of the method 600 of FIG. 6A. In step 650, visible light is emitted from the light source 255 and received at the light receptor 257 while the distal end of the EWC 230 navigates to the target following the pathway plan. In step 655, the light receptor 257 receives and sends visible light reflected from the airway of the lung to the computing device 120, which in turn performs spectroscopic analysis on the reflected visible light using a predictive algorithm in step 660. The reflected light has information such as amplitude and delayed time from the transmission to the reception. The computing device 120 processes the information to determine the density or type of the lung tissue and/or determine whether there are new targets (i.e., diseased or cancerous cells to be treated, mucus, or foreign objects in the airway) not found in the CT scan images.

In step 665, it is determined whether there is a new target along the pathway plan to the target. When it is determined that there is a new target, in step 670, the new target is identified and registered to the 3D model for later treatments. In step 675, the route to the new target, which is a part of the pathway plan to the target, is also saved as a pathway plan to the new target. Then, the method 635 goes back to step 665 to check whether there is another new target.

When it is determined that there is no new target in step 665, the computing device 120 may generate images based on the processed reflected light. Since most of wavelengths of the visible light are reflected from the inside surface of the airway of the lung tissue, the generated images show inside of the bronchial trees. The generated images also show a diseased or cancerous cells, mucus, or foreign objects residing inside of the bronchial tree. In an aspect, when a treatment device penetrates the target for treatment purposes, the generated images can show whether the treatment device is at the target.

In step 685, the generated images are integrated into the 3D model or 2D images derived therefrom based on the location of the EM sensor 265 and the offset distance $D_{OFF}$ between the EM sensor 265 and the light source 255 and light receptor 257. In embodiment, the generated images may be overlaid on CT scan images so that a lower resolution portion of the CT scan images may be replaced with a higher resolution images (i.e., the generated visible images) the light based image data may be selectively fused to create a composite image data set, or the data can be incorporated into the CT image data. In step 690, the computing device displays the generated images with the 3D model or simply the integrated 3D model. These steps 650-690 of navigation are repeated until the target is reached as shown in the method 600 of FIG. 6A.

Figure 6C:
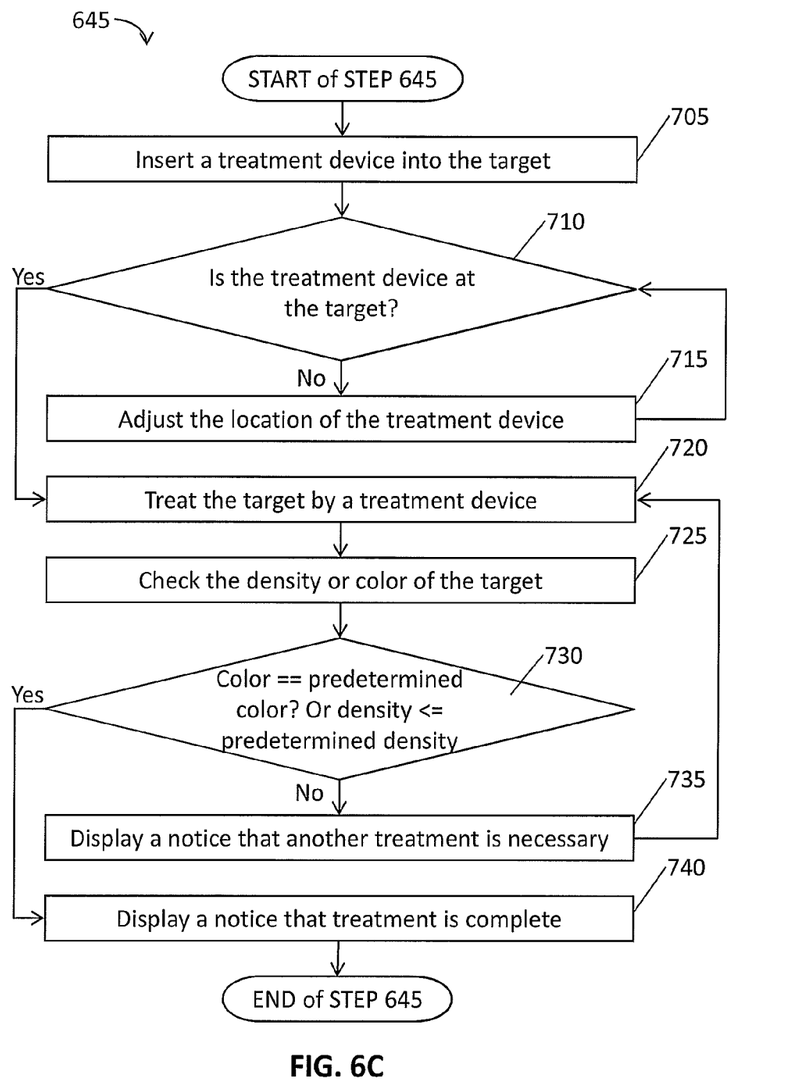
FIG. 6C is a flowchart of a method for checking the level of treatment in accordance with an embodiment of the present disclosure.

In an embodiment, visualization or interrogation using light based techniques as described herein may be used to determine the sufficiency of a treatment. Generally, when one treatment is performed on a target, the attributes of the target including size, density, and water content of the target are altered. Thus, in order to check whether the treatment is complete, the attributes of the target must be checked and compared to similar measurements taken before treatment. In an embodiment, light-based interrogation may be used to determine the level of treatment in combination with the use of fluorescent dyes, which either change color or disappear following sufficient treatment. FIG. 6C illustrates a flowchart of a method for checking the sufficiency of treatment. In step 705, a treatment device, such as an ablation catheter, is inserted into the EWC 230 after removal of the LG 220 and the EM sensor 265. In step 710, it is determined whether the treatment device is at the target by interrogating the tissue as described above.

When it is determined that the treatment device is not at the target, the treatment device is inserted or retreated more or less to adjust its location in step 715. Then, in step 710, the location of the treatment device is again checked. When it is determined that the treatment device is located at the target in step 710, the treatment device treats the target.

In another embodiment, similar steps as steps 705-715 of FIG. 6C may be applied for biopsy. When a biopsy tool is inserted to take samples of the target, the light source 255 and light receptor 257 are used to check whether the biopsy tool is at the correct location of the target. When it is determined that the biopsy tool is at the right place, then the biopsy tool takes samples. When it is determined that the biopsy tools is not at the target, the biopsy tool may be adjusted to reach correctly at the target.

In step 720, the treatment device treats the target. Following treatment application, the light source 255 then emits visible light to interrogate the target and the light receptor 257 receives reflected visible light to determine the attributes of the target in step 725 (e.g., size, color, etc.) and compares the attributes with threshold values in step 730. Here, the threshold values may be predetermined based on a type of disease and may indicate that the disease is treated completely.

When it is determined that the color of the target is not equal to the predetermined color and the density of the target is greater than the predetermined density, the computing device 120 notifies a clinician of incomplete treatment by displaying on the display screen such notice in step 735. The predetermined density may be predetermined based on the density of normal tissue. The method 645 then goes back to step 720 for another treatment. These steps 720-735 repeat until the treatment is complete.

When it is determined that the color of the treated target has achieved a desired change in color in a case of using fluorescent dyes, or when it is determined that the density of the target is less than or equal to the predetermined density in step 730, the computing device 120 notifies a clinician of complete treatment by displaying that the treatment is complete in step 740 and the method 645 of checking the sufficiency of treatment is ended.

In embodiments, step 730 may determine whether an airway become sufficiently large. Generally, asthma is caused by narrow airway. Airways become narrow, clogged, or restricted due to mucus, foreign objects, or swollen smooth tissue. Treatment may be enlarging the airway by removing mucus or foreign objects or subduing the swollen smooth tissue. In this embodiment, the size of the airway is compared with the size of airway prior to the treatment. The other steps of checking may apply similarly.

In another embodiment, the monitoring device 130 and/or the computing device 120 may display a color code on the display, notifying a clinician of a status. The status may be based on a location of the EWC 230 of the catheter guide assembly 110. The status may indicate whether the EWC 230 of the catheter guide assembly 110 is located at a not-in-target location, at the target, or at a location adjacent to healthy tissue, and whether treatment of the target is complete. For example, the color code may be used in a way that a red color indicates that the EWC 230 is at a not-in-target location, a green color indicates that the EWC 230 is at a target, a yellow color indicates that the EWC 230 is adjacent to healthy tissue, and an orange color indicates that the treatment is complete. However, this is an example and is not meant to limit the scope of this disclosure. Other status indication systems may be employed as people in the ordinary skill in the art would apprehend.

Though not described in detail above, with respect to FIG. 1, the network interface 128 enables other computing devices, the bronchoscope 115, and the catheter guide assembly 110 to communicate through a wired and/or wireless network connection. In FIG. 1, the bronchoscope 115 and catheter guide assembly 110 may transmit or receive medical images, medical data, and control data to and from the computing device 120 via a wired connection. In a case where the network interface 128 connects to other computing devices or the bronchoscope 115 and catheter guide assembly 110 wirelessly, the network interface 128 uses a frequency for communication, which may be different from the frequency the bronchoscope 115 or the catheter guide assembly 110 uses for transmitting the captured images.

The memory 126 of computing device 120 may include one or more among solid-state storage devices, flash memory chips, mass storage, tape drive, or any computer-readable storage medium which is connected to a processor through a storage controller and a communications bus. Computer readable storage media include non-transitory, volatile, non-volatile, removable, and non-removable media implemented in any method or technology for storage of information such as computer-readable instructions, data structures, program modules or other data. For example, computer-readable storage media includes random access memory (RAM), read-only memory (ROM), erasable programmable read only memory (EPROM), electrically erasable programmable read only memory (EEPROM), flash memory or other solid state memory technology, CD-ROM, DVD or other optical storage, magnetic cassettes, magnetic tape, magnetic disk storage or other magnetic storage devices, or any other medium which can be used to store desired information and which can be accessed by the computing device 120.

In embodiments, the display 122 may work as an input device such that the display may receive multiple finger actions, such as pinching or spreading fingers. For example, when fingers are pinched, the portion of the displayed image, where the fingers are located on the display 122 before pinching, may be zoomed out and, when fingers are spread, the portion of the lung, where the fingers are located on the display 122 before spreading, is zoomed in. Or when multiple fingers swipe the display 122 together in one direction, the displayed image may be rotated in the same direction as the swiping direction and the amount of rotation is proportional to a distance and/or a speed of the swiping motion. These features may be also implemented using the input device 129.

The input device 129 is used for inputting data or control information, such as setting values, or text information. The input device 129 includes a keyboard, mouse, scanning devices, or other data input devices. The input device 129 may be further used to manipulate displayed images or the 3D model to zoom in and out, and rotate in any direction.

The monitoring device 130 is operatively connected with the bronchoscope 115 and the computing device 120. The monitoring device 130 includes buttons and switches for setting settable items of the monitoring device 130. The monitoring device 130 may be touch-sensitive and/or voice-activated, enabling the monitoring device 130 to serve as both an input and output device. Thus, settable items of the monitoring device 130 may be set, changed, or adjusted by using the buttons, touches to the screen of the monitoring device 130, or voices.

When the bronchoscope 115 captures images of the luminal network of the lung and the captured images do not need to be processed for visualization for human eyes, the monitoring device 130 may receive and display the captured images on the monitoring device 130 so that a clinician may confirm that the location of the catheter guide assembly 110 is in an intended place, particularly for use in confirmation of registration.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

What is claimed is:

1. A system for light-based interrogation comprising:
 a memory storing a pre-procedural three-dimensional (3D) model of a luminal network and a pathway plan illustrating a pathway in the pre-procedural 3D model to a target identified in the pre-procedural 3D model, wherein the pre-procedural 3D model is made of a plurality of two dimensional (2D) images, which are from computed tomography scanning, magnetic resonance imaging (MRI), fluoroscopic imaging, or X-ray imaging;
 an electromagnetic (EM) board configured to generate an EM field;
 an extended working channel (EWC) configured to navigate a luminal network of a patient toward the target in accordance with the pathway plan;
 an EM sensor located at a distal portion of a medical device, which is extending distally from a distal end of the EWC, and configured to sense the EM field;
 a light source located at the distal portion of the EWC and configured to emit light;
 a light receptor located at the distal portion of the EWC and configured to sense light reflected from airway of the luminal network; and
 a processor configured to convert the reflected light into light based data and identify one or more physiological features, generate a visible image, and generate an intra-procedural 3D model by replacing at least one of the plurality of 2D images of the pre-procedural 3D model at a location that corresponds to a detected location of the EM sensor with the visible image, the intra-procedural 3D model generated based on a pre-determined offset between the EM sensor and the light receptor.

2. The system according to claim 1, further comprising a display device configured to display the light based data with the pre-procedural 3D model.

3. The system according to claim 2, wherein the display device is further configured to display a status based on the location of the EM sensor.

4. The system according to claim 3, wherein the status indicates whether the EM sensor is located at a not-in-target location, the target, or a location adjacent to healthy tissue.

5. The system according to claim 3, wherein the status indicates whether treatment of the target is complete.

6. The system according to claim 2, wherein the generated visible images show an interior of the luminal network.

7. The system according to claim 1, wherein a resolution of the generated visible images is finer than a resolution of the pre-procedural 3D model at the location.

8. The system according to claim 1, wherein the visible images are generated from the light based data.

9. The system according to claim 1, wherein the processor is further configured to determine whether a treatment device is at the target based on the light based data.

10. The system according to claim 1, wherein the processor is further configured to determine a sufficiency of treatment based on a density of the target according to the light based data.

11. The system according to claim 1, wherein the processor is further configured to determine a sufficiency of treatment based on a change in fluorescence of the target which is dyed with a fluorescent dye.

12. The system according to claim 1, wherein the processor performs a spectroscopy analysis using a predictive algorithm based on reflections patterns of the light from lung tissue.

13. The system according to claim 1, wherein the light source and the light receptor are integrated into a confocal imaging device or an optical coherence tomographic device.

14. The system according to claim 1, further comprising a plurality of reference sensors located on a patient and configured to recognize a breathing pattern of the patient.

15. The system according to claim 14, further comprising a tracking device configured to identify a location of the EM sensor by compensating for patient's breathing based on the breathing pattern.

16. The system according to claim 1, wherein the generated visible images are selectively fused to create a composite image data set with the pre-procedural 3D model.

17. The system according to claim 1, wherein the emitted light wavelength ranges from 400 nanometer to 700 nanometer.

18. The system according to claim 1, wherein the physiological features are selected from the group consisting of a type of tissue, a density of tissue, or presence of one or more blood vessel.

* * * * *